US006841516B2

(12) United States Patent
Johal et al.

(10) Patent No.: US 6,841,516 B2
(45) Date of Patent: Jan. 11, 2005

(54) ROOT RETARDANT

(75) Inventors: Sarjit Johal, Iowa City, IA (US); Richard L. Antrim, Solon, IA (US)

(73) Assignee: Grain Processing Corp., Muscatine, IA (US)

(*) Notice: Subject to any disclaimer, the term of this patent is extended or adjusted under 35 U.S.C. 154(b) by 0 days.

(21) Appl. No.: 10/089,496

(22) PCT Filed: Jul. 30, 2001

(86) PCT No.: PCT/US01/23880

§ 371 (c)(1),
(2), (4) Date: May 1, 2002

(87) PCT Pub. No.: WO02/10331

PCT Pub. Date: Feb. 7, 2002

(65) Prior Publication Data

US 2003/0060369 A1 Mar. 27, 2003

Related U.S. Application Data

(60) Provisional application No. 60/221,830, filed on Jul. 28, 2000.

(51) Int. Cl.$^7$ .......................... A01N 37/36; A01N 65/00

(52) U.S. Cl. ....................... 504/117; 504/142; 504/320; 426/592

(58) Field of Search ................................ 504/117, 320, 504/142, 116.1; 426/592

(56) References Cited

U.S. PATENT DOCUMENTS

| | | |
|---|---|---|
| 2,903,399 A | 9/1959 | Dixon |
| 3,188,279 A | 6/1965 | Kneen et al. |
| 3,320,696 A | 5/1967 | Wright et al. |
| 3,556,946 A | 1/1971 | Polen |
| 5,030,268 A | 7/1991 | Christians |
| 5,290,749 A | 3/1994 | Christians et al. |
| 5,290,757 A | 3/1994 | Christians et al. |
| 5,573,997 A | 11/1996 | Lojek |
| 5,622,743 A | 4/1997 | Tanaka et al. |

FOREIGN PATENT DOCUMENTS

| | | |
|---|---|---|
| WO | WO 94/16053 | 7/1994 |
| WO | WO 00/255595 | 5/2000 |

OTHER PUBLICATIONS

Cook, A.H. et al., "Chemical Aspects of Malting. II. Method for Assaying the Germination–Inhibitory Activity of Barley Steeping Liquors", *J. Inst. Brewing*, 1952, 58: 407–13, Abstract.

Peers et al., "Germination Inhibitory Substances in Oat Husk", *W. African J. Bio. Chem.*, 1958, 2: 9–14, Abstract.

Adkins et al., "The Physiological Basis of Seed Dormancy in Avena Fatua", *Crop Science Plant Ecol.* 1985, 310–16, Abstract.

Missen et al., "Metabolism of Sinapis Alba Seeds in Water Under Anaerobic Conditions", *Phytochemistry*, 1970, 1473–18, Abstract.

A. H. Cook et al., "Method for Assaying the Germination–Inhibitory Activity of Barley Steeping Liquors", *J. Inst. Brewing*, 1952, 407–413.

K.T. Luu et al., "Characterization of Inhibitory Substances of Tall Fescue on Birdsfoot Trefoil", *Crop Science*, 29, 1989, 407–412.

Griffiths et al., "Retardation of Modification and Enzyme Formation in Barley Endosperm by Steep Liquors and Other Substances",*J. Inst. Brewing*, 1962.

Matsushima et al., "Physiological Activities of Zeanic Acid, a New Plant–Growth Promotor from Corn Steep Liquor", 1972, Publication of University of Tokyo, Japan, pp 1873–1880.

Matsushima et al., "Isolatin of Zeanic Acid, a Natural Plant Growth–regulator from Corn Steep Liquor and its Chemical Structure", 1972, Publication of Sankyo Co., Ltd. Tokyo, Japan, pp 1865–1871.

"Isolation of a New Quinoline, 2,8–Dihydroxycinchoninic Acid from Corn Steep Liquor", *Agr. Bio. Chem*, vol. 34, No. 9, 1970, pp 1430–1431.

Evenari, "Germination Inhibitors", *The Botanical Review*, 1949, vol. XV, Hebrew University, Jerusalem.

*Primary Examiner*—S. Mark Clardy
(74) *Attorney, Agent, or Firm*—Banner & Witcoff, Ltd.

(57) ABSTRACT

The present invention provides a method of retarding rootlet formation from one or more plants in a medium that can support the growth thereof, which method includes introducing into the medium a growth inhibiting effective amount of a growth inhibitor which comprises corn steep liquor. In other embodiments, the growth inhibitor is a mixture of a growth medium and lactic acid. In preferred embodiments, the present invention further provides a malting composition that includes a fermentable grain and a growth inhibitor, wherein the growth inhibitor is present in an amount effective to retard rootlet formation.

8 Claims, No Drawings

ROOT RETARDANT

TECHNICAL FIELD OF THE INVENTION

This invention pertains to root retardants. In some embodiments, the invention is in the field of malting compositions and methods, such as in preparing fermented beverages.

BACKGROUND OF THE INVENTION

There is an ongoing effort to identify and develop new herbicides, particularly naturally occurring substances having root retardant activity. However, the identification of commercially viable retardants from abundant natural resources has proven to be rather difficult. Some active compounds derived from natural sources have been identified. For example, U.S. Pat. No. 5,290,749 ("the '749 patent") describes the use of corn protein hydrolysates, which are produced by enzymatic hydrolysis of corn gluten meal, for inhibiting the germination of weeds. U.S. Pat. No. 5,290,757 ("the '757 patent") describes various dipeptides as having herbicidal activity. These applications have not been commercially exploited, however, possibly due to the apparent high cost per active dose that would be required to for commercially viable applications. The successful commercialization of non-toxic, natural materials for such applications requires a large, inexpensive, readily available source of the active agent.

Corn gluten meal, an insoluble product obtained from the processing of corn, is presently marketed as a root retardant, and is described in U.S. Pat. No. 5,030,268. However, the herbicidal potency of corn gluten meal per unit weight of solids is relatively weak, requiring the application of a somewhat large quantity of the material relative to the medium in order to achieve desirable herbicidal efficacy. As such, there is a need for more potent, non-toxic, commercially viable natural materials.

One industry in which a particular need for cost-effective naturally produced herbicides is found in the brewing industry. Generally, beer and other fermentable beverages are prepared by malting a fermentable grain (often barley) and subsequently fermenting the malted grain. During the malting step, enzymes in the grain cause the breakdown of other components of the grain into maltose. Usually, however, the malting of the grain undesirably causes emergent growth of rootlets from the grain. The rootlets thus generated generally must be removed prior to fermentation, thus requiring additional processing costs and adversely affecting yields. The malting techniques known in the art are not satisfactory in inhibiting rootlet growth prior to fermentation.

In light of the foregoing, it is a general object of the invention to provide a root retardant. In some embodiments, it is an object to provide a malting composition that includes a root retardant and a maltable grain. The present invention provides such herbicides and methods of using them. These and other advantages of the present invention, as well as additional inventive features, will be apparent from the description of the invention provided herein.

SUMMARY OF THE INVENTION

Surprisingly, it is now been discovered that corn steep liquor, *lactobacillus* broth, and the addition product of the deMan-Rosola-Sharpe ("MRS") medium, as described in deMan et al., "A Medium for the Cultivation of Lactobacilli," *J. App. Bact.*, 23:130 (1960) and lactic acid can serve as root retardants.

In one embodiment, the invention provides a method for malting, whereby a fermentable grain, such as barley, is malted in the presence of sufficient root retardant to inhibit rootlet formation of the fermentable grain. Also provided by the invention is a malting composition and a method for fermentation.

Other features and embodiments of the invention are set forth hereinbelow and in the appended claims.

DESCRIPTION OF THE PREFERRED EMBODIMENTS

The invention contemplates the use of a product that has root retardant activity. One such medium is a *lactobacillus* broth, for instance, a broth comprising the fermentation product of MRS medium. The MRS medium is a complex medium that includes proteose peptone number 3, beef extract, yeast extract, dextrose, polysorbate 80, ammonium citrate, sodium acetate, magnesium sulfate, manganese sulfate, and dipotassium phosphate. Any suitable lactic acid producing bacteria may be employed in connection with the invention. Preferred bacterial species include *Lactobacillus delbrueckii* sp. *lactis* (ATCC 4797) and *Lactobacillus delbrueckii* sp. *delbrueckii* (ATCC 4996).

In accordance with another embodiment of the invention, lactic acid is added to the MRS medium to form a growth medium. When the growth medium is fermented, the fermentation preferably is allowed to proceed to an extent such that essentially all dextrose is consumed. When lactic acid is added, lactic acid preferably is added in an amount ranging from about 1 to about 5% by w/v. It is contemplated that the majority of the lactic acid in the composition will be present in the form of a salt. The pH of the product preferably is in the range of about 4 to 8, but may be outside this range.

In a preferred embodiment, the growth inhibitor of the present invention includes a composition that is selected from the group consisting of corn steep liquor concentrates, dried corn steep liquor and combinations thereof. In a particularly preferred embodiment, the growth inhibitor of the present invention consists essentially of corn steep liquor (also referred to as corn steep water) or a concentrate thereof (e.g., corn steep liquor concentrate, dried corn steep liquor, and the like). The corn steep liquor used in accordance with the present invention is preferably native, unprocessed or nominally processed corn steep liquor.

Corn steep liquor (CSL), also referred to as corn steep water, is used almost exclusively in feed and in certain commercial fermentation applications as a nutrient source. Consequently, it is an underutilized, inexpensive by-product of the corn wet milling processing. The use of CSL, particularly native CSL, provides a large, inexpensive, readily available source of nonselective, herbicidal activity.

Typically, the initial step in the corn wet milling process involves steeping shelled corn in water containing sulfur dioxide and lactic acid bacteria for 30–50 hours. The purpose of the steeping procedure is to soften the kernel for removal of the shell and thus permit grinding and fractionation of the various kernel components. The liquor recovered after steeping is generally referred to as thin corn steep liquor or corn steep water.

The steeping process, while undertaken specifically to prepare the kernel for grinding, spawns other incidental events, the most noteworthy of which is the leaching of various biomolecules, metabolites and minerals into the water. The lactic acid bacteria present in the CSL metabolize some of the leached compounds and concomitantly release other metabolites and into the mixture. Thus, corn steep liquor (CSL) is a complex broth composed of carbohydrates, proteins (e.g., polypeptides and amino acids), organic acids (e.g., lactic acid and phytic acid), nucleic acids, minerals and bacteria. A common industry-wide practice is to concentrate the thin corn steep liquor by evaporation to a solids content of about 50%. It has been shown, for example, that corn steep liquor in various concentrations has root retardant activity against barley.

It is believed that the method of the present invention also can be applied toward the post emergent growth inhibition of one or more postemergent plants. The term "postemergent growth" as utilized herein refers to post-germination plant growth that is generally understood to correspond to the visible "emergence" of the plant from the medium. Postemergent plants thus include, for example, plants that have undergone significant root formation, plants that have undergone significant sprout formation, plants having one or more sprouts that have exited the surface of a soil medium, plants having undergone root formation to the extent that the roots can support a soil-emergent sprout, and the like. Accordingly, the present invention further provides a method of inhibiting the further growth of a postemergent plant in a medium that can support the growth thereof, which method includes introducing into the medium a postemergent growth inhibiting effective amount of a growth inhibitor as described hereinabove.

CSL contains valuable nutrients such as, for example, nitrogen, phosphate and minerals which can promote the growth and health of certain desirable ("wanted") postemergent annual and perennial plants. As such, the invention relates to the use of corn steep liquor and the other materials discussed above as a nonselective, preemergent herbicide for the growth inhibition of undesirable ("unwanted") plants and, optionally, as a nutrient that can simultaneously promote the growth of desirable ("wanted") postemergent plants.

Accordingly, the present invention is also drawn to a method of inhibiting the preemergent growth of a plant in a medium that further comprises one or more postemergent plants. When the medium comprises one or more postemergent plants, the growth inhibitor can be introduced into the medium in an amount which is effective to inhibit the growth and also effective to promote the growth of the one or more postemergent plants in the medium. When a postemergent plant is present in the medium, it is preferably a postemergent plant selected from the group consisting of a fruit, a vegetable, an ornamental plant, a turf grass, and a grain. For instance, the postemergent plant may be a potted fruit, such as tomatoes or strawberries, an ornamental plant, such as a flower or orchid, a vegetable, such as onions or broccoli, an exotic plant, and so forth.

The invention finds particular applicability in connection with malting, more particularly, in connection with the brewing industry. By "malting" it is contemplated the formation of maltose in a maltable grain, generally via complex biochemical processes believed to involve enzymatic action. Generally, a grain is malted by steeping of the grain such that the grain imbibes water, followed by a period in which the grain germinates, and most often followed by kilning of the grain.

While malting may be employed for purposes other than brewing (for example, in the preparation of confectionaries), malting most often is employed in connection with the preparation of fermented beverages, most typically beer. Innumerable varieties and styles of beer and similar fermented beverages are known, these include, for instance, lagers, such as pilsners, Dortmunder, Munich, and steam; malt liquors; weissbiers; bock beers; ales; stouts; porters; spruce beers; honey ales; and mulled ales;. While innumerable brewing methodologies are known, generally the malted grain is milled and mashed to form a wort. The wort is then boiled; in this step, adjuncts such as hops, corn syrup, starch, or other ingredients may be added. After the wort is cooled, it is fermented to form a fermented beverage. Commercially, several additional steps are performed, including maturation of the fermented beverage, cooling (to cause precipitation of protein-tannin complexes), filtration and/or pasteurization, and containering, i.e., storage of the beverage in a bottle, keg, or can. In the fermentation process of the invention, other steps may be added, and in some cases, steps may be omitted. Moreover, not all of the steps are always performed by the same entity; for instance, malting may be performed by a maltster, and the malted barley or other grain may be transported to a brewer for fermentation.

In accordance with the invention, the root retardant may be used in connection with a malting and/or fermentation process. For instance, the invention encompassing a malting composition that includes a maltable or fermentable grain and a root retardant, the root retardant being present in an amount effective to inhibit rootlet formation during germination. The invention further contemplates a method of malting, including selecting as a root retardant one of the compositions is discussed hereinabove, forming a malting composition, and malting the malting composition. Those skilled in the art will be able to appreciate the extent of malting desired in any given application, but generally speaking, the malting should proceed to an extent sufficient to form maltose in the amount desired. The invention further contemplates a fermentation method which contemplates fermenting a malted malting composition thus prepared.

The following examples further illustrate the present invention but should not be construed as in any way limiting its scope.

EXAMPLE 1

This example demonstrates the preemergent growth inhibiting activity of corn steep liquor as compared to that of a corn protein hydrolysate.

The corn protein hydrolysate (CPH) used in this example was prepared in accordance with Example 1 of U.S. Pat. No. 5,290,749. The corn steep liquor (CSL) used in this example was a refrigerated concentrate obtained directly from a commercial corn wet milling process line.

The seeds were prepared as follows. Commercial barley seeds (grade B) were prepared by soaking them in water for approximately 24 hours prior to assay initiation. The water imbibed seeds were then damp dried using paper towels. The assays were initiated about 2–4 hours after the treatment.

The germination assays were carried out as follows. Test solutions were mixed with the prepared barley seeds (10 ml of test solution per 100 g of prepared barley seeds) for about 1–2 minutes. The seeds were then spread out on two layers of damp paper towels and covered with a layer of damp paper towels. The covered, treated seeds were incubated on a laboratory bench at room temperature for about 40 hours. The assay results are shown below in Table 1.

TABLE 1

| Test Solution | Test Solution Dry Solids (% by weight) | Percent Growth Inhibition | Observations |
|---|---|---|---|
| Control (Distilled Water) | 0 | 0 | |
| CPH | 2.5 | 0 | Equal or better growth than control |
| CPH | 5 | 10 | Comparable to control |
| CSL (Whole) | 7 | 50 | Growth substantially lower than control |
| CSL (Whole) | 14.5 | 80–90 | Very little root growth |
| CSL (Whole) | 27.1 | 100 | No root growth |
| CSL (Supernate Only)[1] | 13.9 | 80 | More growth than whole broth at equivalent solids content |
| CSL (Supernate Only)[1] | 27.5 | 90 | Several rootlets noted, otherwise devoid of growth |

[1]Supernatant recovered by centrifugation to remove insoluble materials.

The foregoing data demonstrates the superior plant growth inhibiting activity of corn steep liquor. For example, the 50% percent growth inhibition of barley treated with CSL whole broth at 7% solids was significantly greater than the 10% growth inhibition of barley treated with CPH at 5% solids.

EXAMPLE 2

This example demonstrates the growth inhibiting activity of corn steep liquor (CSL) and corn gluten liquor ("overs") as compared to corn protein hydrolysate (CPH). The CPH and CSL were obtained in accordance with Example 1. The dried corn gluten liquor sample, also referred to as "overs," was recovered from an in-line process centrifuge during concentration of the insoluble corn gluten process stream. The collected "overs," which are devoid of gluten, were then concentrated either by evaporation (EVAP) or reverse osmosis (RO). The concentrates were dried by spray-drying.

Barley seeds were prepared and subjected to germination assays in accordance with Example 1. The assay results are shown below in Table 2.

TABLE 2

| Test Solution | Dry Solids (% by weight) | Percent Growth Inhibition | Observations |
|---|---|---|---|
| Control - distilled water | 0 | 0 | |
| CPH | 5 | 5–10% | Nominal inhibition, about equal to control |
| CPH | 10 | 15–20% | Slightly better than control |
| "overs" (EVAP) | 5 | 15–20% | Equal to or slightly better than CPH |
| "overs" (EVAP) | 10 | 30–40% | Clear, visible inhibition |
| "overs" (RO) | 5 | 15–20% | Growth substantially lower than control |
| "overs" (RO) | 10 | 30–40% | Several rootlets noted, otherwise devoid of growth |
| CSL | 7 | 50% | Several rootlets noted, otherwise devoid of growth |
| CSL | 14.5 | 90% | |

This example demonstrates the plant growth inhibiting activity of corn solubles. Although some plant growth inhibiting activity resides in the overs, it has significantly lower activity than that found in CSL.

EXAMPLE 3

This example demonstrates the growth inhibiting activity of CSL, at various concentrations and pHs, against a number of different seeds. The corn steep liquor (CSL) used in this example was obtained in accordance with Example 1 and was diluted with distilled water to produce two different solids concentrations, specifically, solutions having solids concentrations of 5% and 12% by weight on a dry solids basis (dsb). The 5% dsb and 12% dsb solutions were separated into two groups, one of which was adjusted to pH 4, and the other adjusted to pH 8.

The following seeds were tested: ryegrass, buckwheat, rye, oats, mustard, and cucumber. Each of the four solutions described above (7-ml aliquots each) was applied to filter paper measuring approximately 38 $cm^2$. Each treated filter paper was housed in a sterile petri dish. Seeds (about 20–40) of each of the foregoing plants were placed on the treated filter papers. Germinated seeds were tallied after about 5 days of incubation at room temperature. The assay results are shown below in Tables 3–8.

TABLE 3

Ryegrass

| CSL Concentration (dsb) | pH | % Germination |
|---|---|---|
| Control (water) | | 74 |
| 12.5% | 4 | 0 |
| 12.5% | 8 | 0 |
| 5% | 4 | 0 |
| 5% | 8 | 0 |

TABLE 4

Buckwheat

| CSL Concentration (dsb) | pH | % Germination |
|---|---|---|
| Control (water) | | 80 |
| 12.5% | 4 | 0 |
| 12.5% | 8 | 0 |
| 5% | 4 | 0 |
| 5% | 8 | 0 |

TABLE 5

Rye (Winter)

| CSL Concentration (dsb) | pH | % Germination |
|---|---|---|
| Control (water) | | 100 |
| 12.5% | 4 | 0 |
| 12.5% | 8 | 0 |
| 5% | 4 | 8 (Strong growth inhibition) |
| 5% | 8 | 14 (Growth inhibited) |

TABLE 6

Oats

| CSL Concentration (dsb) | pH | % Germination |
|---|---|---|
| Control (water) | | 50 |
| 12.5% | 4 | 0 |
| 12.5% | 8 | 0 |
| 5% | 4 | 0 |
| 5% | 8 | 0 |

TABLE 7

Cucumber

| CSL Concentration (dsb) | pH | % Germination |
|---|---|---|
| Control (water) | | 94 |
| 12.5% | 4 | 0 |
| 12.5% | 8 | 0 |
| 5% | 4 | 0 |
| 5% | 8 | 0 |

TABLE 8

Mustard

| CSL Concentration (dsb) | pH | % Germination |
|---|---|---|
| Control (water) | | 88 |
| 12.5% | 4 | 0 |
| 12.5% | 8 | 0 |
| 5% | 4 | 0 |
| 5% | 8 | 0 |

The foregoing data demonstrates the potent growth inhibiting activity of corn steep liquor against a variety of different plants. The compositions are active at pH 4 and at pH 8, and at 5% and 12.5% concentrations (dsb) in each pH range.

EXAMPLE 4

Lactic acid bacteria broth was produced by inoculating about two hundred and fifty millimeters of sterile Lactobacilli MRS media (Becton Dickinson Microbiology System, Spraks, Md.) with *Lactobacillus delbrueckii* sp. *lactis* (ATCC 4797) in separate shake flasks. The inoculated shake flasks were incubated in a walk-in incubator for about 48 hours. Upon examination, clear visual evidence of bacterial growth was apparent.

After removing from the incubator, one flask was set aside. The other flask was autoclaved at 121° C., 15 psi, for about 20 minutes and cooled to room temperature. The samples were found to have a solids content of about 5% and a pH of 4.2.

Root retardant activity was assayed using barley seeds. Commercial barley seeds (Robust, Grade B) were prepared by soaking in water for approximately 24 prior to assay initiation. The water-imbibed seeds were then damp dried using paper towels and incubated for about 20 hours at room temperature.

The test solutions were mixed with the prepared barley seeds (10 ml of test solution per 100 grams of prepared barley seeds) for 1 to 2 minutes. The seeds were then spread out on damp paper towels and covered with additional damp paper towels to maintain a high moisture environment. The covered, treated seeds were incubated on a laboratory bench at room temperature for about 40 hours, then assayed to determine herbicidal activity. The assay results are shown in Table 9.

TABLE 9

| Sample | Inhibition Score* |
|---|---|
| Water (Control) | 0 |
| 0.05% (dsb) lactobacillus broth | 0 |
| 0.1% (dsb) lactobacillus broth | 2 |
| 0.25% (dsb) lactobacillus broth | 8 |
| 0.25% (dsb) lactobacillus broth** | |
| 0.5% (dsb) lactobacillus broth | 10 |
| 0.5% (dsb) lactobacillus broth** | |
| MRS Broth/Growth media | 1 |
| 0.6% (dsb) CSL | 2 |
| 1.2% (dsb) CSL | 9 |

*Visual Score based on rootlet growth where 0 = No inhibition and 10 = Total inhibition
**Autoclaved The results of this experiment demonstrate that *lactobacillus* shake flask culture broth possesses substantial germination inhibition activity. On a percent solids basis whole (unprocessed) *lactobacillus* broth, which is about 5% solids, exhibits almost 2.5 times the activity of corn steep liquor. Moreover, the observed activity is heat-resistant, as evidenced by the finding that autoclaved broth is fully active. Cell viability also does not appear to be contributing factor. The autoclaved sample, for example displays the same level of activity as the sample that was not autoclaved.

EXAMPLE 5

This example illustrates the dose dependent effect of lactic acid bacteria fermentation broth on barley seedling germination as assessed by commercial malt quality control standards. The materials, procedures and conditions employed in this example are the same as those routinely practiced in the malt industry. The studies, which used a six-row commercial barley variety, proceeded according to the following procedures.

a) Barley was washed and steeped in water for about 24 hours and processed as per standard industry practices;

b) The water imbibed seeds, which had 'chitted' (i.e., rootlet growth point exposed) at this point, were incubated for another approximately 20 hours to allow for further biochemical and physiological development;

c) The steeped and incubated barley, which was now exhibiting a "forked" rootlet appearance, was rinsed in the respective *lactobacillus* broth (LBB) solutions and incubated for another two or three days with periodic watering as necessary;

d) Following the incubation period, the processed barley was kilned;

e) The dried barley was then ground, screened and evaluated;

f) The findings of this study are shown in Table 10.

TABLE 10

| Analysis | Control | 0.05% LBB Solids | 0.07% LBB Solids |
|---|---|---|---|
| Moisture % | 4.4 | 4.0 | 4.3 |
| Extract % Fine Grand, As Is | 75.6 | 76.1 | 75.7 |
| Extract % Fine Grind, Dry Basis | 79.1 | 79.2 | 79.1 |
| Extract % Course Grind, As Is | 74.5 | 75 | 74.0 |
| Extract % Course Grind, Dry Basis | 77.9 | 76.1 | 77.4 |
| Difference, % Fine-Course Extracts | 1.2 | 1.1 | 1.7 |

TABLE 10-continued

| Analysis | Control | 0.05% LBB Solids | 0.07% LBB Solids |
|---|---|---|---|
| Conversion Time, Minutes | 5 Min. | 5 Min. | 5 Min. |
| Speed of Filtration | Normal | Normal | Normal |
| Color of Wort, Degree Lovibond | 1.69 | 1.98 | 1.95 |
| Carity of Wort & Hach Turbidity Reading | Clear | Clear | Clear |
| Diastatic Power, Degrees, Dry Basis | 166 | 163 | 154 |
| Alpha Amylase Units, 20 C, Dry Basis | 42.3 | 53.4 | 47.7 |
| Total Malt Protein, % Dry Basis | 12.4 | 12.2 | 12.6 |
| Soluble Malt Protein, % Dry Basis | 6.01 | 5.98 | 5.57 |
| Ratio, S/T Malt Protein | 48.7 | 48.9 | 44.1 |
| Wort Viscosity, c.p. | 1.42 | 1.43 | 1.47 |
| Beta Glucan | 234.7 | 240.9 | 314.6 |
| Final Sample Total Weight - Malt (gm) | 1725.4 | 1727.7 | 1728.6 |
| Final Total Weight- Rootlets (gm) | 80.8.6 | 74.8 | 67.3 |
| Ratio-Rootlets to Malt (%) | 4.68% | 4.33% | 3.89% (few, short rootlets) |

This example illustrates that, in addition to the visible lactic acid bacteria-induced phenotypic changes such as the reduced rootlet growth and seed softening, biochemical changes usually associated with the malting process are measurably affected by the low solids, *lactobacillus* broth solutions. These biochemical changes measurably alter the physiochemical attributes of the malt as demonstrated by changes in the quality control (QC) parameters monitored by the malt suppliers and customers.

EXAMPLE 6

This example evaluates the performance of *lactobacillus* broth (LBB), *lactobacillus* plus a commercial agricultural sticker (surfactant) (a modified phthalic alkyd from Olympic Chemical, Mainland, Pa.), corn steep liquor (CSL), corn steel liquor plus a commercial agricultural sticker and several *lactobacillus*, CSL and herbicidal corn gluten mixtures. The specific formulations tested were as follows:

a) Corn steel liquor (CSL). This formulation was prepared by diluting CSL (about 45% solids) that was obtained directly from a commercial corn wet milling line to about 20% solids with water.

b) Corn steep liquor plus sticker. A commercial sticker was added to the aforementioned CSL solution (20% dsb) at the recommended label rate.

c) *Lactobacillus* broth was produced in shake flask culture using *Lactobacillus delbrueckii* sp. *lactis* (ATCC 4797) and MRS media. The whole broth had a solids content of about 4.8% and a pH of about 4.3.

d) *Lactobacillus* broth (about 4.8% solids) blended 1:1 with a CSL solution (about 20% solids). Final solids of solution determined to be about 14%.

Commercially available plastic planting trays were loaded with a professional soil mix at a commercial greenhouse operation. The loaded trays were lightly watered, divided into three sections, and seeded with an estimated quantity of winter rye and ryegrass seeds. Seeds were dispersed on the soil surface and left uncovered. The herbicides were then sprayed using a hand sprayer to the designated section of the tray. The trays were then transferred to and maintained in an environmentally regulated greenhouse. Treatment application rates were based on a pound per acre basis equivalence. For the purposes of this study, the corn steep liquor (CSL), CSL plus *lactobacillus* broth and CSL plus sticker application rate was equivalent to about 560–580 pounds/acre, the *lactobacillus* broth and LBB plus sticker application rate was equivalent to about 150 pounds per acre.

After application, the trays were not watered for about 24 hours. Thereafter, they were watered as needed to keep the soil moist. The trays were routinely watered several times a day.

The trays, which were inspected daily, were monitored and maintained for 2 to 4 weeks post-germination.

The findings of this study are shown in the Table below.

TABLE 11

| Tray Number | Seed Type | Treatment | % Inhibition |
|---|---|---|---|
| 1 | Winter Rye | CSL + Sticker | 70 |
|  |  | Water (Control) | 0 |
|  |  | LBB + Sticker | 65 |
| 2 | Ryegrass | CSL + Sticker | 25 |
|  |  | Water (Control) | 0 |
|  |  | LBB + Sticker | 60 |
| 3 | Winter Rye | CSL | 65 |
|  |  | LBB | 20 |
|  |  | CLS + LBB | 70 |
| 4 | Ryegrass | CSL | 50 |
|  |  | LBB | 20 |
|  |  | CSL + LBB | 65 |

The greenhouse findings indicate that the sticker (surfactant) significantly enhances LBB activity but marginally lowers CSL activity. The difference in effect not unexpected considering the differences in composition and associated physicochemical attributes of *lactobacillus* broth relative to CSL. What is somewhat surprising, however, is the decline in CSL activity especially in regards to ryegrass inhibition. In addition, it is seen that CSL can substitute for the sticker with no concomitant loss in activity. The addition of LBB to CSL may in fact enhance activity.

EXAMPLE 7

This example illustrates that *lactobacillus* broth can be concentrated using heat and vacuum to produce a high solids concentrate that exhibits no detectable loss of germination inhibition activity.

The *lactobacillus* broth was produced using *Lactobacillus delbrueckii* sp. *lactis* (ATCC 4797) shake flask culture and Lactobacilli MRS media. The broth, which was determined to have a solids content of about 4.7% and a pH of about 4.1, was concentrated used a laboratory rotary evaporator (rotovap). Specifically, about 750 mls of whole broth was transferred to a vacuum flask, which was heated to about 80° C. while rotating in a temperature controlled water bath. A low vacuum was then applied to the heated broth and the solution maintained under these conditions for about 80 minutes. Approximately 65 mls of concentrate was retrieved from the flask. The concentrate, which had a solids content of about 52% (dsb) and a pH of about 4.3, was diluted and assayed using the barley seed germination assay described in Example 4. The results are shown in the Table below.

TABLE 12

| Herbicide | % Inhibition |
| --- | --- |
| Water (Control) | 0 |
| 0.25% LBB - Not Concentrated | 40 |
| 0.47% LBB - Not Concentrated | 95 |
| 0.25% - Dil. Conc. | 40 |
| 0.5% - Dil. Conc. | 100 |

As seen, there is little difference in the growth retardant activity by between unconcentrated and heat-mediated evaporative concentrated and high solids LBB.

EXAMPLE 8

Two other lactic acid bacteria cultures, *Lactobacillus delbrueckii* sp. *delbrueckii* (ATCC 4996) and a dry mixed culture comprised of *Lactobacillus plantarum* and *Pediococcus cerevisiae*, a commercial silage inoculant product for the fermentation of forage and high moisture grains, were grown in accordance with the procedures outlined in Example 7. Following approximately 40 hours of growth, the cultures were tested for rootlet inhibition in the activity assay. The activity assay results showed that both the *Lactobacillus delbrueckii* sp. *delbrueckii* (ATCC 4996) and the mixed culture exhibited root retardant activity essentially identical to that observed with *Lactobacillus delbrueckii* sp. *lactis* (ATCC 4797) shown in Table 9 of Example 4.

EXAMPLE 9

This example examines lactic acid:MRS medium contributions to the observed root retardant activity.

The media, Lactobacilli MRS Broth, was prepared as per the manufacturer's instructions, autoclaved, and chilled to room temperature. Herbicides were prepared as follows:

1. The MRS media standard, which had a pH of about 6.5, was used as is.
2. A herbicide composed of MRS+3% lactic acid sample was prepared by adding sufficient lactic acid to an aliquot of MRS broth to bring the final lactic acid concentration to 3%. The pH of this solution was then adjusted to pH 4.2 with NaOH.
3. An acidified MRS media sample was prepared by adjusting the pH of standard media to 4.2 with the addition of HCl.

Rootlet inhibitory activity was assayed used barley seeds. Seed preparation and germination assay procedures were executed as described in Example 7.

The results of this assay are shown in the Table below.

TABLE 13

| Sample | Inhibition Score |
| --- | --- |
| Water (Control) | 0 |
| MRS media | 2 |
| MRS media + 3% lactic acid, pH 4.2 | 9 |
| HCl/acidified MRS media, pH 4.2 | 4 |

This example demonstrates that the addition of 3% lactic acid to the media enhances the rootlet inhibitory activity in a manner that is substantially greater than that achieved by simply acidifying the media alone.

EXAMPLE 10

This example examines the relationship between pH and root retardant activity.

*Lactobacillus* broth was produced as described in Example 7. The finished whole broth, which included the cells, was autoclaved (121° C.; 15 minutes) prior to use and had a pH of about 4.2.

The samples examined for germination inhibitory activity were as follows:

1. *Lactobacillus* broth, pH 4.2.
2. *Lactobacillus* broth diluted 50% with water, pH 4.2.
3. *Lactobacillus* broth, pH 5.5. This was prepared by adding sufficient NaOH to adjust the pH of the finished broth 5.5.
4. *Lactobacillus* broth, pH 5.5, diluted 50% with water.
5. *Lactobacillus* broth, pH 7.8. This was prepared by adding sufficient NaOH to adjust the pH of the finished broth to 7.8.
6. *Lactobacillus* broth, pH 7.8, diluted 50% with water.

Root retardant activity was assayed used barley seeds. Seed preparation and germination assay procedures were executed as described in Examples 7 and 9.

The findings of this study are shown in the Table below.

TABLE 14

| Sample | Inhibition Score |
| --- | --- |
| Water (Control) | 0 |
| Broth, pH 4.2 | 10 |
| Diluted Broth, pH 4.2 | 6 |
| Broth, pH 5.5 | 6 |
| Diluted Broth, pH 5.5 | 3 |
| Broth, pH 7.8 | 7 |
| Diluted Broth, pH 7.8 | 3 |

The results of this study suggest that the *lactobacillus* broth mediated germination inhibitory activity has little pH dependency. Taken together with the findings of Example 9, the results of this experiment imply that several agents may contribute to the germination inhibitory activity.

EXAMPLE 11

In this example the performance of spray-dried yeast treated corn steep liquor (sdCSL) was evaluated against liquid yeast treated corn steep liquor (lCSL) and commercial gluten (Gluten).

The materials and methods (including application rates) were the same as those used in the prior example. Spray-dried yeast treated corn steep liquor (sdCSL) was prepared in a laboratory spray-drier using lCSL as the starting material.

The results of this study are exhibited in the Table below.

TABLE 15

| Tray Number | Seed Type | Treatment | % Inhibition |
| --- | --- | --- | --- |
| 1 | Winter Rye | Water (Control) | 0 |
|   | Ryegrass | Water (Control) | 0 |
| 2 | Winter Rye | lCSL | 55% |
|   | Ryegrass | lCSL | 45% |
| 3 | Winter Rye | sdCSL | 65% |
|   | Ryegrass | sdCSL | 60% |
| 4 | Winter Rye | Gluten | 30% |
|   | Ryegrass | Gluten | 10% |

As seen, there is little difference in the growth retardant activity between liquid or spray-dried material.

Two other commercially available corn steep powders exhibited rootlet-inhibiting activity comparable to materials tested in the aforementioned examples.

EXAMPLE 12

A malting composition is prepared by soaking barley seeds in water and mixing the *lactobacillus* broth prepared in accordance with Example 4.

EXAMPLE 13

A beer is prepared by fermenting the malting composition of Example 12.

Thus, it is seen that the general object of the invention has been satisfied in that a root retardant has been provided. The root retardant is suitable for use in the brewing of fermentable beverages, wherein the herbicide may be used during the malting step to inhibit emergent growth of the grain that is to be fermented.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims. All references cited herein are hereby incorporated by reference in their entireties.

What is claimed is:

1. A method of inhibiting the preemergent growth of a plant in a medium that can support the growth thereof, comprising:
    introducing into said medium a preemergent growth inhibiting amount of a growth inhibitor, said growth inhibitor comprising a lactic-acid-containing steep liquor to which additional lactic acid has been added, said steep liquor having preemergent growth inhibiting activity and said additional lactic acid having been added in an amount effective to enhance the preemergent growth inhibiting activity of said steep liquor.

2. A method according to claim 1, said steep liquor being corn steep liquor.

3. A method for preparing a preemergent herbicide for inhibiting the preemergent growth of a plant in a medium that can support the growth thereof, comprising:
    providing a lactic-acid-containing steep liquor, said steep liquor having preemergent growth inhibiting activity, and
    adding additional lactic acid to said steep liquor, said additional lactic acid being added in an amount effective to enhance the preemergent growth inhibiting activity of said steep liquor.

4. A method according to claim 3, said steep liquor being corn steep liquor.

5. A method according to claim 3, said lactic acid being added in the form of a fermentation product of a lactic-acid-producing bacterium.

6. A method of inhibiting the preemergent growth of a plant in a medium that can support the growth thereof, comprising:
    introducing into said medium a preemergent growth inhibiting amount of a growth inhibitor, said growth inhibitor comprising the deMan-Rosola-Sharpe medium to which lactic acid has been added in an amount effective to enhance the preemergent growth inhibiting activity of said medium.

7. A method for preparing a preemergent herbicide for inhibiting the preemergent growth of a plant in a medium that can support the growth thereof, comprising:
    adding lactic acid to the deMan-Rosola-Sharpe medium in an amount effective to enhance the preemergent growth inhibiting activity of said medium.

8. A method of inhibiting the preemergent growth of a plant in a medium that can support the growth thereof, comprising:
    introducing into said medium a preemergent growth inhibiting amount of a growth inhibitor, said growth inhibitor comprising the lactic acid bacterial fermentation product of the deMan-Rosola-Sharpe medium.

* * * * *